US008774932B2

(12) United States Patent
Fahey

(10) Patent No.: US 8,774,932 B2
(45) Date of Patent: *Jul. 8, 2014

(54) REMOTE HEALTH MONITORING SYSTEM

(71) Applicant: InfoBionic, Inc., Lowell, MA (US)

(72) Inventor: Michael Fahey, Medway, MA (US)

(73) Assignee: Infobionic, Inc., Lowell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/900,335

(22) Filed: May 22, 2013

(65) Prior Publication Data

US 2013/0253354 A1 Sep. 26, 2013

Related U.S. Application Data

(63) Continuation of application No. 13/446,490, filed on Apr. 13, 2012, now Pat. No. 8,478,418.

(60) Provisional application No. 61/476,072, filed on Apr. 15, 2011.

(51) Int. Cl.
| | | |
|---|---|---|
| *A61N 1/08* | (2006.01) | |
| *A61B 5/04* | (2006.01) | |
| *G06F 19/00* | (2011.01) | |
| *A61B 5/00* | (2006.01) | |
| *G08B 21/10* | (2006.01) | |

(52) U.S. Cl.
CPC ............ *G06F 19/3418* (2013.01); *G08B 21/10* (2013.01); *A61B 5/0006* (2013.01)
USPC ................................ 607/60; 607/32; 600/523

(58) Field of Classification Search
USPC ................................ 600/509, 523; 607/32, 60
See application file for complete search history.

(56) References Cited

U.S. PATENT DOCUMENTS

| | | |
|---|---|---|
| 4,721,114 A | 1/1988 | DuFault et al. |
| 4,905,205 A | 2/1990 | Rialan |

(Continued)

FOREIGN PATENT DOCUMENTS

| | | |
|---|---|---|
| EP | 0 959 607 A2 | 11/1999 |
| WO | WO 01/93756 A2 | 12/2001 |

(Continued)

OTHER PUBLICATIONS

International Search Authority, International Search Report and the Written Opinion for international Application No. PCT/US2012/033554 dated Aug. 28, 2012 (15 pages).

(Continued)

*Primary Examiner* — Tammie K Heller
(74) *Attorney, Agent, or Firm* — Bookoff McAndrews, PLLC

(57) ABSTRACT

A data collection system collects and stores physiological data from an ambulatory patient at a high resolution and/or a high data rate ("more detailed data") and sends a low-resolution and/or downsampled version of the data ("less detailed data") to a remote server via a wireless network. The server automatically analyzes the less detailed data to detect an anomaly, such as an arrhythmia. A two-tiered analysis scheme is used, where the first tier is more sensitive and less specific than the second tier. If the more sensitive analysis detects or suspects the anomaly, the server signals the data collector to send more detailed data that corresponds to a time period associated with the anomaly. The more specific second tier analyses the more detailed data to verify the anomaly. The server may also store the received data and make it available to a user, such as via a graphical or tabular display.

24 Claims, 7 Drawing Sheets

(56) References Cited

U.S. PATENT DOCUMENTS

| | | | |
|---|---|---|---|
| 5,502,688 A | 3/1996 | Recchione et al. | |
| 5,564,429 A | 10/1996 | Bornn et al. | |
| 5,678,562 A | 10/1997 | Sellers | |
| 5,876,351 A | 3/1999 | Rohde | |
| 6,049,730 A | 4/2000 | Kristbjarnarson | |
| 6,168,563 B1 | 1/2001 | Brown | |
| 6,225,901 B1 | 5/2001 | Kail, IV | |
| 6,366,871 B1 | 4/2002 | Geva | |
| 6,389,308 B1 | 5/2002 | Shusterman | |
| 6,416,471 B1 | 7/2002 | Kumar et al. | |
| 6,466,806 B1 | 10/2002 | Geva et al. | |
| 6,471,087 B1 | 10/2002 | Shusterman | |
| 6,494,829 B1 | 12/2002 | New, Jr. et al. | |
| 6,496,731 B1 | 12/2002 | Lovett | |
| 6,569,095 B2 | 5/2003 | Eggers | |
| 6,664,893 B1 | 12/2003 | Eveland et al. | |
| 6,665,385 B2 | 12/2003 | Rogers et al. | |
| 6,694,177 B2 | 2/2004 | Eggers et al. | |
| 6,801,137 B2 | 10/2004 | Eggers | |
| 6,804,558 B2 | 10/2004 | Haller et al. | |
| 6,840,904 B2 | 1/2005 | Goldberg | |
| 6,925,324 B2 | 8/2005 | Shusterman | |
| 6,957,107 B2 | 10/2005 | Rogers et al. | |
| 6,980,112 B2 | 12/2005 | Nee | |
| 7,002,468 B2 | 2/2006 | Eveland et al. | |
| 7,099,715 B2 | 8/2006 | Korzinov et al. | |
| 7,120,485 B2 | 10/2006 | Glass et al. | |
| 7,194,300 B2 | 3/2007 | Korzinov | |
| 7,222,054 B2 | 5/2007 | Geva | |
| 7,343,197 B2 | 3/2008 | Shusterman | |
| 7,542,878 B2 | 6/2009 | Nanikashvili | |
| 7,552,035 B2 | 6/2009 | Cataltepe et al. | |
| 7,580,755 B1 | 8/2009 | Schwartz et al. | |
| 7,587,237 B2 | 9/2009 | Korzinov et al. | |
| 7,630,756 B2 | 12/2009 | Linker | |
| 7,654,965 B2 | 2/2010 | Morganroth | |
| 7,689,439 B2 | 3/2010 | Parker | |
| 7,706,883 B1 | 4/2010 | Singh | |
| 7,729,753 B2 | 6/2010 | Kremliovsky et al. | |
| D621,048 S | 8/2010 | Severe et al. | |
| 7,801,591 B1 | 9/2010 | Shusterman | |
| 7,803,118 B2 | 9/2010 | Reisfeld et al. | |
| 7,803,119 B2 | 9/2010 | Reisfeld | |
| 7,907,996 B2 | 3/2011 | Prystowsky et al. | |
| 7,996,075 B2 | 8/2011 | Korzinov et al. | |
| 7,996,187 B2 | 8/2011 | Nanikashvili et al. | |
| 8,005,546 B1 * | 8/2011 | Levine | 607/32 |
| 8,255,238 B2 | 8/2012 | Powell et al. | |
| 2001/0023360 A1 | 9/2001 | Nelson et al. | |
| 2002/0082665 A1 | 6/2002 | Haller et al. | |
| 2002/0156384 A1 | 10/2002 | Eggers et al. | |
| 2003/0028442 A1 | 2/2003 | Wagstaff et al. | |
| 2003/0122677 A1 | 7/2003 | Kail, IV | |
| 2003/0172940 A1 | 9/2003 | Rogers et al. | |
| 2004/0006278 A1 | 1/2004 | Webb et al. | |
| 2004/0100376 A1 | 5/2004 | Lye et al. | |
| 2004/0172290 A1 | 9/2004 | Leven | |
| 2005/0004486 A1 | 1/2005 | Glass et al. | |
| 2005/0182334 A1 | 8/2005 | Korzinov et al. | |
| 2005/0203349 A1 | 9/2005 | Nanikashvili | |
| 2006/0206066 A1 | 9/2006 | Ferek-Petric | |
| 2007/0073266 A1 | 3/2007 | Chmiel et al. | |
| 2007/0130657 A1 | 6/2007 | Rogers et al. | |
| 2007/0191723 A1 | 8/2007 | Prystowsky | |
| 2007/0208233 A1 | 9/2007 | Kovacs | |
| 2007/0270665 A1 | 11/2007 | Yang et al. | |
| 2007/0276270 A1 | 11/2007 | Tran | |
| 2007/0279217 A1 | 12/2007 | Venkatraman et al. | |
| 2007/0279239 A1 | 12/2007 | Lachenit et al. | |
| 2008/0097550 A1 | 4/2008 | Dicks et al. | |
| 2008/0097551 A1 | 4/2008 | Dicks et al. | |
| 2008/0097552 A1 | 4/2008 | Dicks et al. | |
| 2008/0097793 A1 | 4/2008 | Dicks et al. | |
| 2008/0097908 A1 | 4/2008 | Dicks et al. | |
| 2008/0097909 A1 | 4/2008 | Dicks et al. | |
| 2008/0097910 A1 | 4/2008 | Dicks et al. | |
| 2008/0097911 A1 | 4/2008 | Dicks et al. | |
| 2008/0097912 A1 | 4/2008 | Dicks et al. | |
| 2008/0097913 A1 | 4/2008 | Dicks et al. | |
| 2008/0097914 A1 | 4/2008 | Dicks et al. | |
| 2008/0097917 A1 | 4/2008 | Dicks et al. | |
| 2008/0103370 A1 | 5/2008 | Dicks et al. | |
| 2008/0103554 A1 | 5/2008 | Dicks et al. | |
| 2008/0103555 A1 | 5/2008 | Dicks et al. | |
| 2008/0108907 A1 * | 5/2008 | Stahmann et al. | 600/529 |
| 2008/0183502 A1 | 7/2008 | Dicks et al. | |
| 2008/0215120 A1 | 9/2008 | Dicks et al. | |
| 2008/0215360 A1 | 9/2008 | Dicks et al. | |
| 2008/0218376 A1 | 9/2008 | Dicks et al. | |
| 2008/0224852 A1 | 9/2008 | Dicks et al. | |
| 2009/0076344 A1 | 3/2009 | Libbus et al. | |
| 2009/0076345 A1 | 3/2009 | Manicka et al. | |
| 2009/0076350 A1 | 3/2009 | Bly et al. | |
| 2009/0076405 A1 | 3/2009 | Amurthur et al. | |
| 2009/0099469 A1 | 4/2009 | Flores | |
| 2009/0112769 A1 | 4/2009 | Dicks et al. | |
| 2009/0115628 A1 | 5/2009 | Dicks et al. | |
| 2009/0234672 A1 | 9/2009 | Dicks et al. | |
| 2009/0261968 A1 | 10/2009 | El-Hamamsy et al. | |
| 2009/0275854 A1 | 11/2009 | Zielinski et al. | |
| 2009/0326981 A1 | 12/2009 | Karkanias et al. | |
| 2010/0056881 A1 | 3/2010 | Libbus et al. | |
| 2010/0076325 A1 | 3/2010 | Cho et al. | |
| 2010/0113895 A1 | 5/2010 | Cho et al. | |
| 2010/0198089 A1 | 8/2010 | Litovchick et al. | |
| 2010/0204586 A1 | 8/2010 | Pu et al. | |
| 2010/0249541 A1 | 9/2010 | Geva et al. | |
| 2010/0249625 A1 | 9/2010 | Lin | |
| 2010/0250271 A1 | 9/2010 | Pearce et al. | |
| 2010/0268103 A1 | 10/2010 | McNamara et al. | |
| 2010/0286545 A1 | 11/2010 | Wolfe et al. | |
| 2010/0298664 A1 | 11/2010 | Baumann et al. | |
| 2011/0004072 A1 | 1/2011 | Fletcher et al. | |
| 2011/0009711 A1 | 1/2011 | Nanikashvili | |
| 2011/0066042 A1 | 3/2011 | Pandia et al. | |
| 2011/0066555 A1 | 3/2011 | Dicks et al. | |
| 2011/0078441 A1 | 3/2011 | Dicks et al. | |
| 2011/0090086 A1 | 4/2011 | Dicks et al. | |
| 2011/0093283 A1 | 4/2011 | Dicks et al. | |
| 2011/0093284 A1 | 4/2011 | Dicks et al. | |
| 2011/0093285 A1 | 4/2011 | Dicks et al. | |
| 2011/0093286 A1 | 4/2011 | Dicks et al. | |
| 2011/0093287 A1 | 4/2011 | Dicks et al. | |
| 2011/0093297 A1 | 4/2011 | Dicks et al. | |
| 2011/0097710 A1 | 4/2011 | Macrae et al. | |
| 2011/0098583 A1 | 4/2011 | Pandia et al. | |
| 2011/0144470 A1 | 6/2011 | Mazar et al. | |
| 2011/0158430 A1 | 6/2011 | Dicks et al. | |
| 2011/0161111 A1 | 6/2011 | Dicks et al. | |
| 2011/0166466 A1 | 7/2011 | Chon et al. | |
| 2011/0167250 A1 | 7/2011 | Dicks et al. | |
| 2011/0179405 A1 | 7/2011 | Dicks et al. | |
| 2011/0270049 A1 | 11/2011 | Katra et al. | |
| 2011/0270112 A1 | 11/2011 | Manera et al. | |
| 2011/0301435 A1 | 12/2011 | Albert et al. | |
| 2011/0301439 A1 | 12/2011 | Albert et al. | |
| 2012/0165616 A1 | 6/2012 | Geva et al. | |

FOREIGN PATENT DOCUMENTS

| | | |
|---|---|---|
| WO | WO 01/93756 A3 | 12/2001 |
| WO | WO 02/082799 A2 | 10/2002 |
| WO | WO 02/082799 A3 | 10/2002 |

OTHER PUBLICATIONS

International Search Authority, International Search Report and the Written Opinion for International Application No. PCT/US2012/033592 dated Aug. 31, 2012 (14 pages).

Jovanov et al., "Patient Monitoring Using Personal Area Networks of Wireless Intelligent Sensors," Electrical and Computer Engineering Department, University of Alabama in Huntsville, Biomedical Sciences instrumentation, 37;378-8, 6 pages, 2001.

(56) References Cited

OTHER PUBLICATIONS

Hopley et al., "The Magnificent ROC (Receiver Operating Characteristic Curve)." http://www.anaestheist.com/stats/roc/index.htm, 26 pages, Sep. 21, 2001.
Ghazal et al., "Automatic Classification of Heartbeats Using ECG Morphology and Heartbeat Interval Features," IEEE Transactions on Biomedical Engineering, vol. 51, No, 7, pp. 1196-1206, 11 pages, Jul. 2004.
Philips, "Philips Remote Patient Monitoring," Philips Medical Systems, 4 pages, 2007.
Archive.org, "Clinical Policy Bulletin: Cardiac Event Monitors," No. 0073, Aetna, Inc., web.archive.org_web_20090514063858_http_www.aetna.com_cpb_medical_data_1_99_0073.html, 10 pages, May 14, 2009
Center for Technology and Aging, "Technologies for Remote Patient Monitoring in Older Adults," Center for Technology and Aging, Position Paper, Discussion Draft, 30 pages, Dec. 2009.
Edevice. "M2M Solutions for Home Health Monitoring," edevice, http://www.edevice.com/medical/?gclid=CPCdlfiR_KcCFUpN4AodZEyzgO, 2 pages, 2010.
MedApps, Inc., "MedApps Mobile Wireless Remote Patient Monitoring," http://www.medapps.com/, 3 pages, 2010.
Archive.org, "The Area Under an ROC Curve," http://web.archive.org/web/20100527211847/http://gim.unmc.edu/dxtests/roc3.htm, 2 pages, May 27, 2010.
Medical Biostatistics.com, "Sensitivity-Specificity. Bayes' Rule, and Predictives," MedicalBiostatistics.com, http://www.medicalbiostatistics.com/ROCCurve,pdf. 4 pages. Sep. 5, 2010.
Medical Biostatistics.com, "ROC Curve," MedicalBiostatistics.com, 9 pages, Sep. 25, 2010.
IEEE, "Remote Patient Monitoring Service Using Heterogeneous Wireless Access Networks: Architecture and Optimization" Niyato et al. paper abstract, IEEE Xplore Digital Library http://ieeexplore.ieee.org/xpl/freeabs_all.jsp?arnumber=4909280, 1 page, 2011.
TriMed Media Group, Inc., "FDA Green Lights AirStrip Smartphone Patient Monitoring Tool," TriMed Media Group, Inc., http://cardiovascularbusiness.com/index.php?option=com_articles&article=23414&publication=137&view=portals&form=article23414&limitstart=30, 1 page, 2011.
Google Patents, Google Patent Search: "Healthcare Monitoring "web server" smartphone OR mobile," www.google.com/patents, Mar. 9, 2011, 2 pages.
Wikipedia.org, "Holter Monitor," Wikipedia.org, http://en.wikipedia.org/w/index.php?title=Holter_monitor&oldid=417997699, Mar. 9, 2011, 4 pages.
Aetna, Inc., "Clinical Policy Bulletin: Cardiac Event Monitors," No. 0073, Aetna, Inc., www.aetna.com_cpb_medical_data_1_99_0073.html, 10 pages, Mar. 11, 2011.
Wikipedia.org, "Receiver Operating Characteristic," Wikipedia.org, http://en.wikipedia.org/wiki/Receiver_operating_characteristic, 6 pages, Apr. 14, 2011.
International Searching Authority, Invitation to Pay Additional Fees and, Where Applicable, Protest Fee for International Application No. PCT/US2012/033554, 4 pages, Jul. 3, 2012.
International Searching Authority, Invitation to Pay Additional Fees and Where Applicable, Protest Fee for International Application No, PCT/US2012/033592, 5 pages, Jul. 3, 2012.
Medical Biostatistics.com, "Predictives Based ROC Curve," MedicalBiostatistics.com http://www.medicalbiostatistics.com/PredictivityBasedROC.pdf, 3 pages, Sep. 5, 2012.
International Preliminary Report on Patentability; PCT/US2012/033554; mailed Oct. 15, 2013.
International Preliminary Report on Patentability; PCT/US2012/033592; mailed Oct. 15, 2013.

* cited by examiner

| Setting | Resolution Bits | Sampling rate/second | Transmission Duty Cycle |
|---|---|---|---|
| Low | 12 | 1K | 10's of seconds |
| Medium | 16 | 2K | seconds |
| High | 20 | 4K | sub seconds |
| Real Time | 24 | 32K | Live Streaming |

*FIG. 7*

Table of Example Parameter Measurements Range in Physician's Interface

| Activity Level | Low (Resting) | Moderate (Walking) | Heavy (Running) | Time Window |
|---|---|---|---|---|
| SpO2 | >99% | >99% | >99% | 1 minute |
| Blood Pressure | 110/60 to 140/80 | <140/90 | <150/100 | 5 minutes |
| Respiration | 15-25 | 20/50 | 30-80 | 2 minutes |
| Heart Rate | 50-70 | 60-100 | 80-130 | 30 seconds |

*FIG. 8*

REMOTE HEALTH MONITORING SYSTEM

CROSS REFERENCE TO RELATED APPLICATIONS

This is a continuation application of U.S. patent application Ser. No. 13/446,490, filed Apr. 13, 2012 (now U.S. Pat. No. 8,478,418), which claims the benefit of U.S. Provisional Patent Application No. 61/476,072, filed Apr. 15, 2011, the entire contents of which are hereby incorporated by reference herein.

TECHNICAL FIELD

The present invention relates to remote physiologic monitoring systems and, more particularly, to patient-worn remotely-controlled physiologic monitoring systems.

BACKGROUND ART

Remote monitoring of ambulatory patients enables doctors to detect or diagnose heart problems, such as arrhythmias, that may produce only transient symptoms and, therefore, may not be evident when the patients visit the doctors' offices. Several forms of cardiac event monitors have been used.

A "Holter" monitor is worn by a patient and collects and stores data for a period of time, typically at least 24 hours, and in some cases up to two weeks. After the data has been collected, the Holter monitor is typically brought or sent to a doctor's office, laboratory or the like, and the data is retrieved from the monitor and analyzed. Holter monitors are relatively inexpensive, but they cannot be used for real-time analysis of patient data, because the data is analyzed hours, days or weeks after it has been collected.

More timely analysis of heart data is made possible by pre-symptom (looping memory) event monitors. Such a device collects and stores patient data in a "loop" memory device. The event monitor constantly overwrites previously stored data with newly collected data. The event monitor may include a button, which the patient is instructed to actuate if the patient feels ill or otherwise detects a heart-related anomaly. In response, the event monitor continues to record data for a short period of time and then stops recording, thereby retaining data for a time period that spans the button actuation, i.e., the retained data represents a period of time that extends from (typically) a few minutes before the user actuated the button to (typically) a few minutes after the user actuated the button. The retained data may then be sent via a modem and a telephone connection to a doctor's office or to a laboratory for analysis. Although such an event monitor can facilitate analysis of patient data more proximate in time to the patient-detected anomaly, relying on the patient to actuate the device and then send the data can be problematic.

Some event monitors automatically detect certain arrhythmias and, in response, record electrocardiograph (ECG) data. Automatic event monitors are thought to be more sensitive, but less specific, than manually triggered cardiac event monitors for significant cardiac arrhythmias. However, these devices still rely on patients to send the recorded data for analysis, and there is still a delay between detection of a suspected arrhythmia and transmission of the data.

Mobile cardiovascular telemetry (MCT) refers to a technique that involves noninvasive ambulatory cardiac event monitors that are capable of continuous measurements of heart rate and rhythm over several days. For example, CardioNet, Philadelphia, Pa., provides an MCT device under the trade name "Mobile Cardiac Outpatient Telemetry" (MCOT). The MCOT device includes an automatic ECG arrhythmia detector. The MCOT device couples to a cellular telephone device to immediately transmit automatically detected abnormal ECG waveforms to a remote monitoring center, which can then alert a physician. The MCOT device also includes a memory capable of storing up to 96 hours of ECG waveform data, which can be transmitted over standard telephone lines to the remote monitoring center at the end of each day. Although data about automatically detected arrhythmias are sent immediately to the remote monitoring center, without requiring patient action, the computational resources and corresponding electrical power (battery) required to perform the automatic ECG analysis in the MCOT device are significant.

Some MCT devices continuously send all collected ECG data to a remote monitoring center for analysis. These MCT devices typically do not perform any ECG analysis of their own. Although no patient-initiated action is required, the large amount of data transmitted by the MCT wireless devices congests the wireless channels used to convey the data. Furthermore, a large amount of computational resources is required at the remote monitoring center to analyze the continuous stream of received data, especially when many patients are monitored by a single data center.

U.S. Pat. Publ. No. 2010/0298664 discloses a wireless ECG data collection and analysis system.

U.S. Pat. No. 7,996,187 discloses a personal health monitor that collects and processes physiologic data and wirelessly transmits the processed data to a remote entity.

U.S. Pat. Publ. No. 2009/0076405 discloses a wireless respiration monitoring system. Upon receipt of a notification, a medical provider, a remote monitoring system or a medical treatment device can trigger a higher data sample rate in the patient-worn monitor device and use the higher sample rate data collected thereafter to verify an alert condition.

U.S. Pat. No. 7,801,591 discloses a healthcare information management system that displays patient information at various levels of analysis, based on user need and sophistication level.

SUMMARY OF EMBODIMENTS

An embodiment of the present invention provides a system for remote physiologic monitoring of a body of a patient. The monitoring is performed in association with a remote server. The system includes a plurality of sensors and a transceiver assembly. Each sensor of the plurality of sensors configured to be coupled to the body of the patient to generate respective physiologic data about the body. The transceiver assembly includes a memory, a controller and a wireless transceiver. The transceiver assembly is communicatively coupled to the plurality of sensors. The transceiver assembly is configured to receive the physiologic data from the plurality of sensors. The transceiver assembly is also configured to store the received physiologic data in the memory. The stored data is referred to as "more detailed data." The transceiver assembly is configured to send a subset of the received physiologic data (referred to as "less detailed data"), via the wireless transceiver, to the remote server. The less detailed data sent to the remote server is characterized by: a lower resolution than the more detailed data stored in the memory for a corresponding time period and/or a lower sampling rate than the more detailed data stored in the memory for a corresponding time period and/or having been received from a different set of the sensors than the more detailed data stored in the memory for a corresponding time period. The transceiver assembly is configured to fetch at least a portion of the more detailed physiologic data from the memory, in response to a signal from the remote server. In addition, in response to the signal from the remote server, the transceiver assembly is configured to send the fetched more detailed physiologic data to the remote server.

The less detailed data sent to the remote server may be characterized by a lower resolution than the more detailed data stored in the memory for a corresponding time period and/or a lower sampling rate than the more detailed data stored in the memory for a corresponding time period.

The remote server may be configured to receive the less detailed physiologic data sent by the transceiver assembly and automatically analyze the received less detailed physiologic data for an indication of a health-related anomaly. If the health-related anomaly is indicated, the remote server may be configured to automatically send the signal to the transceiver assembly.

The health-related anomaly may be or include an arrhythmia.

The remote server may also be configured to receive the more detailed physiologic data and automatically analyze the received more detailed physiologic data to verify the indicated health-related anomaly.

The remote server may be configured to analyze the less detailed physiologic data according to a first analytic technique and analyze the more detailed physiologic data according to a second analytic technique. The second analytic technique may have a higher specificity for the health-related anomaly than the first analytic technique.

The remote server may be configured to automatically analyze the received less detailed physiologic data for the indication of the health-related anomaly using ECG data and automatically analyze the received more detailed physiologic data to verify the indicated health-related anomaly using data other than ECG data.

The remote server may be configured to display a first user interface configured to accept at least one user-specified criterion. The remote server may be configured to automatically analyze the received less detailed physiologic data for the indication of the health-related anomaly, based on at least a portion of the less detailed physiologic data meeting the user-specified criterion.

The remote server may be configured to display a first user interface configured to accept at least one user-specified criterion and automatically analyze the received more detailed physiologic data to verify the indicated health-related anomaly, based on at least a portion of the more detailed physiologic data meeting the user-specified criterion.

The wireless transceiver may include a cellular telephone.

The wireless transceiver assembly may include a cellular telephone coupled via a short-range wireless link to the wireless transceiver. The cellular telephone may be configured to: store the more detailed data in the memory; send the less detailed data to the remote server; responsive to the signal, fetch the at least the portion of the more detailed physiologic data from the memory and send the fetched more detailed physiologic data to the remote server via a wireless carrier network.

The system may also include a cellular telephone configured to be communicatively coupled to a wireless carrier network. The cellular telephone may be configured to receive the physiologic data sent by the transceiver assembly via the wireless transceiver and send the received physiologic data via the wireless carrier network to the remote server.

The system may also include an application program configured to be executed by a cellular telephone that is configured to be communicatively coupled to a wireless carrier network. The application program may be configured to receive the physiologic data sent by the transceiver assembly via the wireless transceiver and send the received physiologic data via the wireless carrier network to the remote server.

The plurality of sensors may include an ECG sensor and at least one accelerometer. The remote server may be configured to calculate a respiration rate, based at least in part on data from the ECG sensor and data from the at least one accelerometer.

The remote server may be configured to calculate a first candidate respiration rate, based on the data from the ECG sensor and calculate a second candidate respiration rate based on the data from the at least one accelerometer. If a difference between the first and second candidate respiration rates is less than a predetermined value, the remote server may calculate the respiration rate as an average of the first and second candidate respiration rates. If both the first and second candidate respiration rates are within a predetermined range, the remote server may calculate the respiration rate as being equal to the first candidate respiration rate. If only the first candidate respiration rate is within the predetermined range, the remote server may calculate the respiration rate as being equal to the first candidate respiration rate. If only the second candidate respiration rate is within the predetermined range, the remote server may calculate the respiration rate as being equal to the second candidate respiration rate.

The remote server may be configured to accept, through a first user interface, a user-specified data collection parameter. In response to accepting the user-specified data collection parameter, the remote server may be configured to send the data collection parameter to the transceiver assembly. The transceiver assembly may be configured to receive the data collection parameter and, in response to receipt of the data collection parameter, to change the resolution and/or the sampling rate of the less detailed physiologic data thereafter sent to the remote server.

The remote server may be configured to generate a first display, in a first user interface, from the less detailed physiologic data received from the transceiver assembly. In response to a user input, the remote server may be configured to generate a second display, in the first user interface, from at least a portion of the more detailed physiologic data received from the transceiver assembly and corresponding to a time associated with the data displayed in the first display.

The remote server may be further configured, in response to the user input, to send the signal to the transceiver assembly.

Another embodiment of the present invention provides a method for remote physiologic monitoring of a body of a patient. According to the method, physiologic data is received from a plurality of sensors coupled to the body of the patient. The received physiologic data is stored in a memory. The stored data is referred to as "more detailed data." A subset of the received physiologic data (referred to as "less detailed data") is wirelessly sent to a remote server. The less detailed data sent to the remote server is characterized by: a lower resolution than the more detailed data stored in the memory for a corresponding time period and/or a lower sampling rate than the more detailed data stored in the memory for a corresponding time period and/or having been received from a different set of the sensors than the more detailed data stored in the memory for a corresponding time period. Responsive to a signal from the remote server, at least a portion of the more detailed physiologic data is fetched from the memory. The fetched more detailed physiologic data is sent to the remote server.

The less detailed data sent to the remote server may be characterized by: a lower resolution than the more detailed data stored in the memory for a corresponding time period and/or a lower sampling rate than the more detailed data stored in the memory for a corresponding time period.

In addition, the less detailed physiologic data may be received at the remote server. The received less detailed physiologic data may be automatically analyzed for an indication of a health-related anomaly. If the health-related anomaly is indicated, the signal may be automatically sent.

The more detailed physiologic data may be received and the received more detailed physiologic data may be automatically analyzed to verify the indicated health-related anomaly.

Analyzing the less detailed physiologic data may include analyzing the less detailed data according to a first analytic technique. Analyzing the more detailed physiologic data may include analyzing the more detailed data according to a second analytic technique. The second analytic technique may have a higher specificity for the health-related anomaly than the first analytic technique.

Yet another embodiment of the present invention provides a system for remote physiologic monitoring of a body of a patient. The monitoring is performed in association with a remote server. The system includes a plurality of sensors and a transmitter assembly. Each sensor of the plurality of sensors is configured to be coupled to the body of the patient to generate respective physiologic data about the body. The transmitter assembly includes a memory, a controller and a wireless transmitter. The transmitter assembly is communicatively coupled to the plurality of sensors. The transmitter assembly is configured to receive the physiologic data from the plurality of sensors and store the received physiologic data in the memory. The stored physiologic data is referred to as "more detailed data." The transmitter assembly is also configured to automatically analyze a subset of the received physiologic data (referred to as "less detailed data") for an indication of a health-related anomaly. The less detailed data is characterized by: a lower resolution than the more detailed data stored in the memory for a corresponding time period and/or a lower sampling rate than the more detailed data stored in the memory for a corresponding time period and/or having been received from a different set of the sensors than the more detailed data stored in the memory for a corresponding time period. If the health-related anomaly is indicated, the transmitter assembly is configured to automatically fetch at least a portion of the more detailed physiologic data from the memory and send the fetched more detailed physiologic data to the remote server.

The less detailed data may be characterized by at least one of: a lower resolution than the more detailed data stored in the memory for a corresponding time period and/or a lower sampling rate than the more detailed data stored in the memory for a corresponding time period.

The remote server may be configured to receive the more detailed physiologic data and automatically analyze the received more detailed physiologic data to verify the indicated health-related anomaly.

The transmitter assembly may be configured to analyze the less detailed physiologic data according to a first analytic technique, and the remote server may be configured to analyze the more detailed physiologic data according to a second analytic technique. The second analytic technique may have a higher specificity for the health-related anomaly than the first analytic technique.

BRIEF DESCRIPTION OF THE DRAWINGS

The invention will be more fully understood by referring to the following Detailed Description of Specific Embodiments in conjunction with the Drawings, of which:

FIG. 7 contains a table of exemplary resolutions, sample rates and transmission duty cycles, according to an embodiment of the present invention.

FIG. 8 contains a table that lists exemplary threshold values for several patient activity levels, according to an embodiment of the present invention.

DETAILED DESCRIPTION OF SPECIFIC EMBODIMENTS

In accordance with embodiments of the present invention, methods and apparatus are disclosed for locally collecting and locally storing physiologic data from an ambulatory patient, wirelessly sending only a proper subset of the collected data to a remote central server and there automatically analyzing the sent data in real time. The sent subset of the collected data is less detailed than the data collected and stored by a local patient-attached data collector.

The central server employs a two-tiered analysis methodology. If the first tier, which performs a high-sensitivity but low-specificity analysis, detects a possible arrhythmia in the received subset of the collected data, the server requests the data collector to retrospectively send more detailed data the collector previously stored, i.e., more detailed data from around the time of the suspected arrhythmia.

The second tier performs a high-specificity analysis of the more detailed data to confirm or refute ("verify") the suspected arrhythmia. Thus, overall utilization of the wireless channel used to send the data is kept low by sending detailed data only when necessary to verify a suspected arrhythmia. Furthermore, electrical power (battery) and computational resource requirements of the patient-attached data collector are kept low, because the data collector performs no data analysis.

Thus, significantly, embodiments of the present invention enable the remote server to operate primarily on a less detailed subset of collected data and retrospectively obtain more detailed data when necessary to verify a suspected arrhythmia. In contrast, no known prior art ambulatory patient monitor stores detailed collected data locally and sends only a subset of the collected data to a remote server. No known prior art remote server requests more detailed data from an earlier time period ("retrospectively requests data") in response to detecting a suspected arrhythmia and then uses the more detailed data to verify the suspected arrhythmia.

A "subset" of the collected data means less than all of the collected data. The subset may, for example, be a down-sampled (lower sampling rate) or quantized (less accurate samples) version of the collected data. The subset may include data from one or more sensors or one or more types of data, such as heart rate, ECG waveform, respiration rate, SpO2, blood pressure, body movement (such as provided by accelerometers). The more detailed data may include data from all the same, some of the same or different sensors or different types of data. SpO2 is a measure of the amount of oxygen attached to hemoglobin cells in circulating blood system. SpO2 is typically given as a percentage, normal is around 96%. The "S" in SpO2 stands for "saturation."

Figure 1:
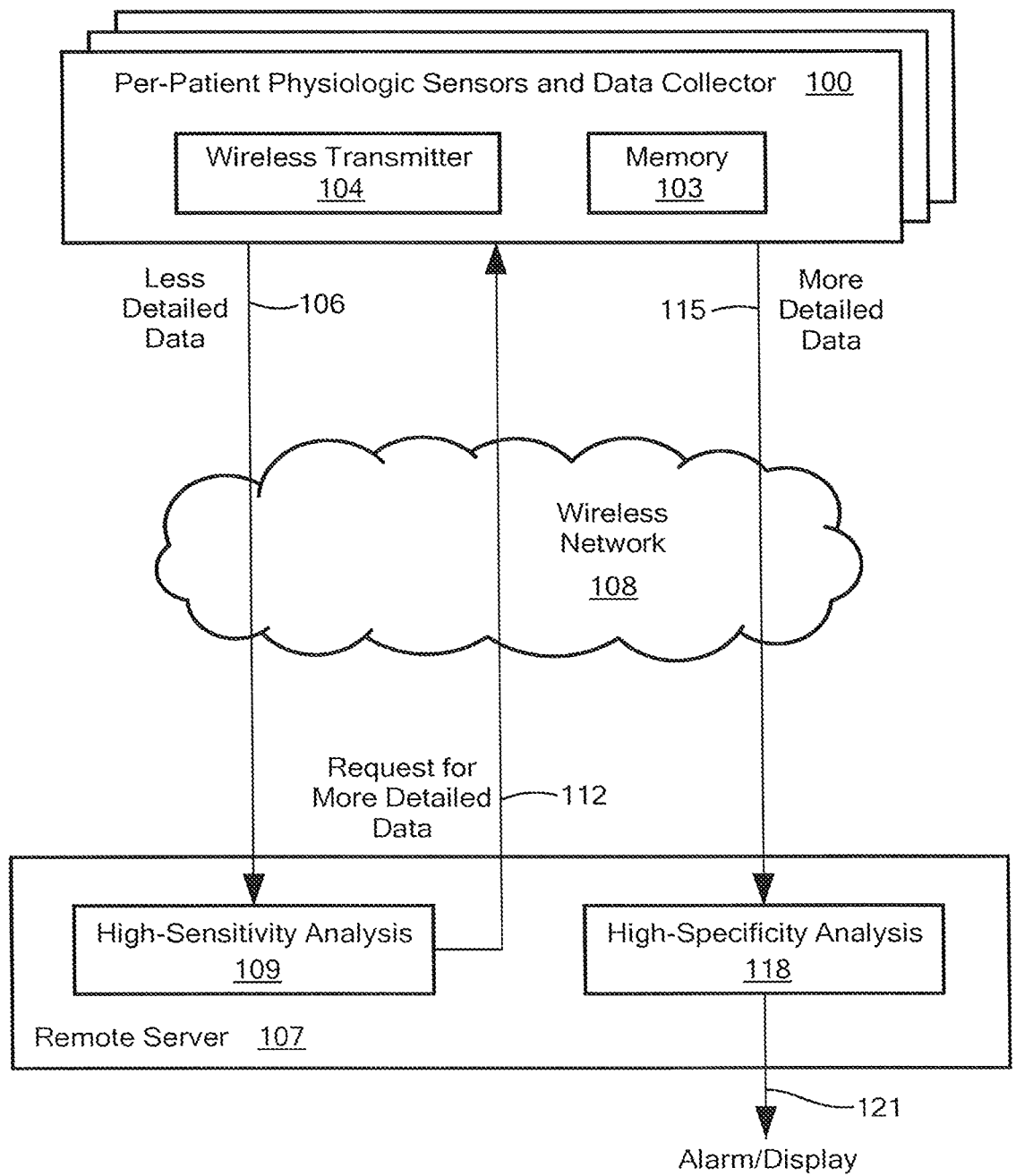
FIG. 1 is a schematic block diagram of an embodiment of the present invention.

FIG. 1 is a schematic block diagram of an embodiment of the present invention. A data collector and set of physiologic sensors (collectively identified at 100) is assigned to each monitored patient. The physiologic sensors are attached to the patient, and data collected from the sensors are stored in a memory 103 within the data collector 100. Time stamps, corresponding to times at which the data were collected, or other suitable data timing information is also stored in the memory 103. If the memory 103 becomes full or reaches a predetermined fullness, the data collector 100 begins overwriting previously stored data, beginning with the oldest data. Thus, the memory 103 stores the most recently collected data on a rolling basis.

The data collector 100 includes, or is coupled to, a suitable wireless transceiver 104, such as a cellular telephone. A subset of the collected data (identified as "less detailed data" 106), including information about when the data were collected, is sent wirelessly to a central remote server 107, such as via a cellular telephone network 108. The less detailed data 106 may be a downsampled version of the collected data. That is, the less detailed data 106 may have a lower sampling rate than the collected and stored data. For example, only every Nth sample of the collected data may be included in the less detailed data 106, where N is an integer or rational fraction that provides a sampling rate sufficient for the first tier analysis. Optionally or alternatively, the less detailed data 106 may be a quantized version of the collected data. That is, the less detailed data 106 may be rounded or otherwise include fewer digits of accuracy than the collected data, although sufficient for the first tier analysis.

The central server 107 may serve many per-patient data collectors 100. The central server 107 performs a high-sensitivity analysis 109 of the less detailed data 106. The high-sensitivity analysis 109 is configured such that it has a low probability of generating a false negative result. That is, the high-sensitivity analysis 109 is not likely to fail to detect an actual arrhythmia. However, to achieve this high level of sensitivity, the high-sensitivity analysis 109 is likely to generate a relatively large number of false positive results, i.e., the first analytical tier may have low specificity.

A relatively large number of false positive results is, however, acceptable for several reasons, including only a relatively small subset of the collected physiological data is sent via the wireless channel 108, thereby conserving the wireless channel's carrying capacity. Conserving wireless channel carrying capacity may be important to support a large number of per-patient data collectors 100 over the wireless channel 108 and/or to enable the wireless channel 108 to carry other types of traffic, such as text messages, streaming video and voice telephone calls, most or all of which may be unrelated to the physiological monitoring described here. Thus, at least conceptually, false positives are traded, at least in part, for increased wireless channel capacity. Furthermore, the bulk or all of the false positives are filtered out by the second tier of analysis, as described next.

If the high-sensitivity analysis 109 detects a suspected arrhythmia, the high-sensitivity analysis 109 sends a request 112 to the data collector 100. The request 112 identifies a time period of interest, such as a time period surrounding the time at which the data that lead to the suspicion were collected. In response to the request 112, the data collector 100 fetches more detailed data for the requested time period from the memory 103 and sends the more detailed data 115 to the central server 107, and then a high-specificity analysis 118 is performed on the more detailed data 115. Preferably, the second analytical tier 118 is also high in sensitivity, so it has a low probability of generating a false negative result.

The high-specificity analysis 118 is configured such that it has a low probability of generating false positive results. That is, the high-specificity analysis 118 is not likely to indicate an arrhythmia when none actually occurred. If the high-specificity analysis 118 verifies that an arrhythmia occurred, an alarm may be raised or information may be displayed 121, such as to alert a physician or technician.

In order to provide results with high specificity and high sensitivity, the high-specificity analysis 118 needs the more detailed data 115, as well as typically consuming more computational resources than the high-sensitivity analysis 109. Requesting 112 and sending 115 the more detailed data utilizes a portion of the wireless channel capacity. However, this utilization occurs only relatively infrequently, i.e., when the high-sensitivity analysis 109 detects a suspected arrhythmia. In addition, the high-specificity analysis 118 consumes a relatively large amount of computational resources. Again, however, this consumption occurs only relatively infrequently.

Thus, the two-tiered analysis 109 and 118 can be seen, at least conceptually, as a tradeoff between, on one hand, complexity involving two separate analysis tiers and occasional high wireless channel and computation resource utilization and, on the other hand, an overall reduction of wireless channel and computational resource utilization. The overall scheme disclosed herein requires fewer computational resources, and correspondingly less power (battery), on the per-patient data collector 100 than prior art schemes that attempt to analyze the collected data at the per-patient device and notify a central system only when an arrhythmia is detected. In addition, the overall scheme uses less wireless channel capacity and fewer central analysis server resources than prior art systems that send constant streams of all collected data to a central server for analysis.

Furthermore, the overall scheme is well suited for implementation in a "cloud computing" environment, where computing resources are available on demand. Thus, in some embodiments, the additional computational resources required for the high-specificity analysis 118 need not be pre-allocated and, therefore, idle most of the time. Instead, computational resources for the high-specificity analysis 118 can be dynamically and automatically utilized, requested or scheduled whenever they are required. Such a cloud computing environment is available from Amazon Web Services LLC under the trade name Amazon Elastic Compute Cloud (Amazon EC2) and RightScale cloud management from RightScale, Inc.

Figure 2:
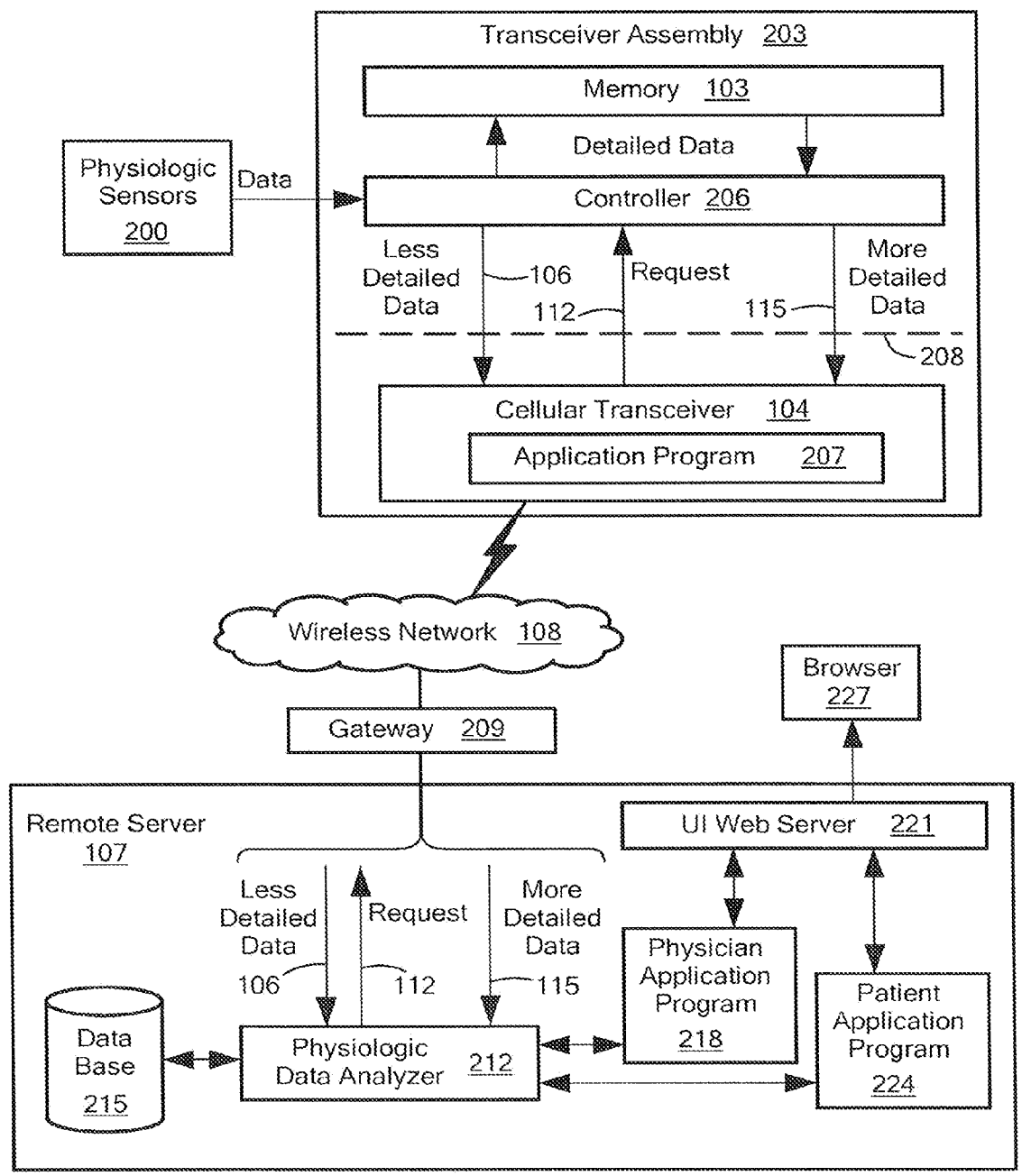
FIG. 2 is a more detailed schematic block diagram of an embodiment of the present invention.

FIG. 2 is a schematic block diagram of an embodiment of the present invention, showing more detail than FIG. 1. One or more physiological sensors 200 are coupled to a transceiver assembly 203. The coupling may be provided by via a short-range wireless system, such as Bluetooth transceivers. Alternatively, the coupling may be provided by wires or optical cable. The transceiver assembly 203 includes a memory 103 and a long-range wireless transceiver 104, such as a cellular telephone transceiver, as discussed above. The long-range wireless transceiver 104 may be replaced by any suitable wireless transceiver, such as a WiFi transceiver (not shown).

A controller 206 directs operation of the transceiver assembly 203. The controller 206 may be implemented by a microprocessor executing instructions stored in a memory, such as the memory 103 or another memory. The controller 206 receives data from the sensors 200 and stores the received data in the memory 103. The controller 206 also provides a less detailed version 106 of the sensor data to the long-range wireless transceiver 104 for transmission, via the wireless network 108, to the remote server 107. The controller 206 may be coupled to the long-range wireless transceiver 104 via wires, optical cables or a short-range wireless system, such as Bluetooth.

Optionally or alternatively, part or all of the functions of the controller 206 and the memory 103 may be implemented by a processor and a memory within the long-range wireless transceiver 104. For example, a "smart phone" may store and execute an application program (software) 207 configured to receive the data from the sensors 200, store the received sensor data in a memory of the smart phone and transmit a subset of the collected data to the remote server 107. In response to the request 112 from the remote server 107, the application program 207 may fetch the more detailed data 115 and send it to the remote server 107. Furthermore, the application program 207 may alter, such as in response to commands from the remote server 107, data collection parameters, such as sampling rate and sampling precision, and data transmission parameters, such as sampling rate and sampling precision of the less detailed data 106 and of the more detailed data 115, as well as transmission packet size, packet transmission rate, number of samples per packet, etc.

The controller 206 and the long-range wireless transceiver 104 should check authenticity of each other and authority to receive data and to be controlled by each other, prior to engaging in substantive communications, transmission of sensor data, control, etc. Furthermore, data and control communications, particularly wireless communications, between and among components of embodiments should be encrypted. For example, wireless data communications between the sensors 200 and the controller 206, between the controller 206 and the long-range wireless transceiver 104 and between the long-range wireless transceiver 104 and the remote server 107 should be suitably encrypted, such as to protect patient privacy.

The transceiver assembly 203 may be implemented as one physical assembly. Alternatively, the transceiver assembly 203 may be implemented as two physically separable components, one component including the controller 206 and the memory 103, and the other component including the long-range wireless transceiver 104. Such a two-part division is indicated by dashed line 208. The two components may communicate with each other via a short-range wireless system, such as Bluetooth (not shown). The tasks of receiving the data from the sensors 200, storing the received data in the memory 103 or in a memory in a smart phone and generating the less detailed data 106 from the collected data may be divided or allocated between the controller 206 and the smart phone.

A suitable gateway 209, as well as other well-known computer networking equipment, such as network switches, routers, firewalls and the like, may be used to couple the remote server 107 to the wireless network 108. The remote server 107 includes a physiological data analyzer 212, which is configured to perform the high-sensitivity analysis 109 and the high-specificity analysis 118 discussed above, with respect to FIG. 1. The remote server 107 may include a database 215, and the data analyzer 212 may be configured to store the received less detailed data 106 and/or the received more detailed data 115, or a portion thereof, in the database 215. The data may be stored in the database 215 in an encrypted form to increase security of the data against unauthorized access.

A physician application program 218 allows a physician to control parameters of the system, such as threshold values used by the data analyzer 212 in performing the high-sensitivity 109 and/or the high-specificity 118 analyses. Optionally, the physician application program 218 also allows the physician to set operating parameters of the transceiver assembly 203, such as the amount by which the less detailed data is downsampled, quantized, etc.

The physician application program 218 also displays data to the physician and allows the physician to select types of data to display, time periods of the data to display, levels of data detail to display and other operating parameters of the system. For example, the physician may select a beginning and ending time surrounding a suspected or verified arrhythmia for display. In response to a query by the physician, the physician application program 218 may fetch and display data from the database 215. If the requested data is not available in the database 215, or if the requested data is not available in the database 215 at the level of detail requested by the physician, the physician application program 218 may automatically communicate with the transceiver assembly 203 to fetch the appropriate data in the appropriate amount of detail.

The physician application program 218 may implement appropriate security protocols, such as requiring the physician to enter logon credentials, so as to appropriately limit access to patient data and comply with regulations, such as the Health Insurance Portability and Accountability Act (HIPAA).

A user interface/web server 221 accepts user (physician, patient or administrator) inputs and generates appropriate displays to facilitate user interaction with the physician application program 218 and a similar patient application program 214, described below. The user interface/web server 221 may generate a window-metaphor based computer user interface on a screen (not shown) coupled to the remote server 107, or the user interface/web server 218 may generate web pages that are rendered by a browser 227 executed by a separate user computer (not shown). The web server 221 and the web browser 227 may communicate with each other using an appropriate encrypted protocol, such as Hypertext Transfer Protocol Secure (HTTPS).

The patient application program 224 provides access by a patient to her own data, using appropriate patient logon credentials and an appropriately secured browser connection.

Figure 3:
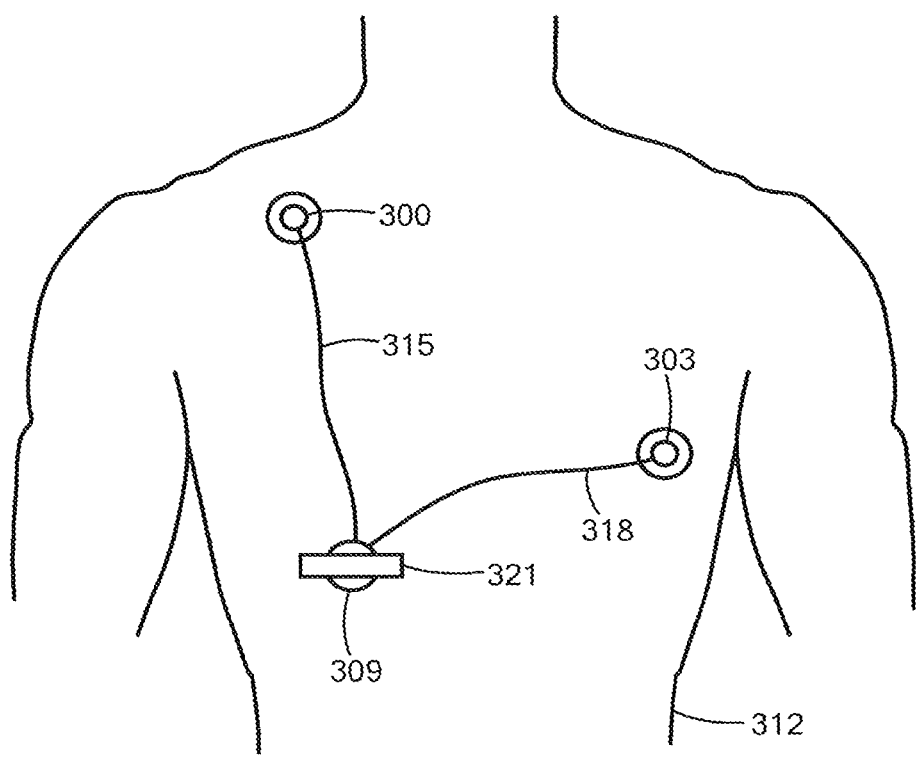
FIG. 3 is a schematic diagram illustrating one possible combination of physiological sensors and a possible placement of the sensors on a torso of a patient, according to an embodiment of the present invention.

FIG. 3 is a schematic diagram illustrating one possible combination of physiological sensors 300, 303 and 309 and a possible placement of the sensors on a torso 312 of a patient. One of the sensors 309 may be attached at about the elevation of the diaphragm of the patient. Each sensor 300-309 may be attached to the torso 312 using well-known gel pads or other conventional attachment techniques. Any combination of well-known physiological electrodes may be used for the sensors 300-309. For example, the sensors 300-309 may include any combination of SpO2 sensors, blood pressure sensors, heart electrodes, respiration sensors, movement and activity sensors, and the like. Movement or activity may be sensed with appropriate accelerometers or gyroscopes, such as micro electro-mechanical system (MEMS) devices. The sensors 300-309 may be connected via wires or optical cables 315 and 318 or via wireless links, such as Bluetooth links Respiration data may be derived from ECG baseline data, as is known to those of skill in the art.

The transceiver assembly 203 (FIG. 2), or a portion thereof, may be attached to, and supported by, one of the sensors 309, as indicated at 321. Optionally, other sensors, such as a patient weight measuring device, blood pressure cuff, etc., may be disconnectably coupled via wires, optical cables or wirelessly to the transceiver assembly 203.

Figure 4:
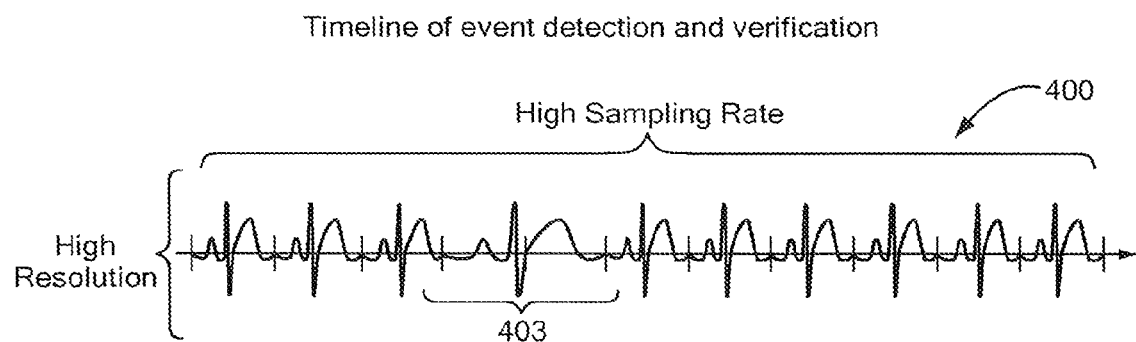
FIG. 4 contains a hypothetical ECG waveform representing detailed data collected from the sensors of FIG. 3 and stored in a memory, according to an embodiment of the present invention.

As noted, the transceiver assembly 203 collects physiologic data, stores the collected data in a memory 103 and sends a less detailed version of the data 106 to the remote server 107. Upon detecting a suspected arrhythmia, the remote server 107 requests 112 more detailed data. FIG. 4 contains a hypothetical ECG waveform 400, representing detailed data collected from the sensors 200 and stored in the memory 103. That is, the collected data has a relatively high sampling rate and a relatively high resolution. Assume the waveform 400 includes a portion 403, during which the waveform is anomalous.

Figure 5:
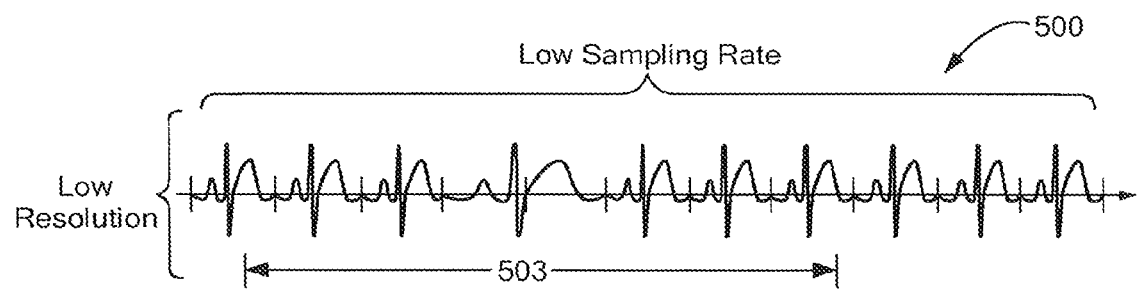
FIG. 5 contains a waveform representing a less detailed version of the data collected from the sensors of FIG. 3 and sent to a remote server, according to an embodiment of the present invention.

FIG. 5 contains a waveform 500, representing a less detailed version 106 of the collected data. The less detailed data 106 is transmitted to the remote server 107. The high-sensitivity analysis 109 (FIG. 1) performed by the data analyzer 212 (FIG. 2) detects the anomaly 403 as a suspected arrhythmia. Responsive to this detection, the data analyzer 212 (FIG. 2) sends a request 112 to the transceiver assembly 203 for more detailed data for a time period 503 around the anomaly 403. The length of the period 503 may depend on the type of anomaly detected by the data analyzer 212. Various types of anomalies, and corresponding time periods 503, may be specified by the physician via the physician application program 218.

Figure 6:
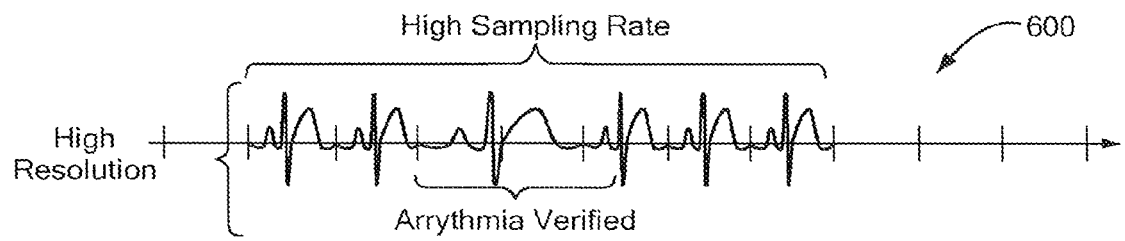
FIG. 6 contains a waveform representing the more detailed data a transceiver assembly sends to the remote server in response to a request from the server, according to an embodiment of the present invention.

FIG. 6 contains a waveform 600, representing the more detailed data 115 (FIG. 2) the transceiver assembly 203 sends to the remote server 107. The more detailed data 115 has a higher sampling rate, higher resolution and/or contains data from more sensors than the less detailed data 106. Using the more detailed data 115, the high-specificity analysis performed by the data analyzer 212 verifies the suspected arrhythmia.

FIG. 7 contains a table 700 of exemplary resolutions, sample rates and transmission duty cycles (times between data transmissions from the transceiver assembly 203 to the remote server 107). Each row of the table 700 represents a different combination of these parameters. Each row is labeled with a "Setting," indicating relative timeliness of the data feed from the transceiver assembly 203, such as based on relative seriousness of the patient's condition. Thus, the transceiver assembly 203 may store more highly resolved data (in terms of the number of bits per sample), more data samples (in terms of the number of samples per second) and/or data from more sensors or more types of sensors than are sent to the remote server 107. Furthermore, the transceiver assembly 203 may store data for a period of time after data representing that time period has been sent to the remote server 107. The specific settings in the table 700 are only examples of what a physician may determine from a range of possible values.

The remote server 107 may be configured to determine data collection parameters, either manually, such as in response to inputs received via the physician application program 218, or automatically, such as in response to collected data meeting one or more predetermined criteria, such as detecting an anomaly in the collected data. A physician may select, via the physician application program 218, one of the sets of data collection parameters shown in table 700, or the physician may specify custom values, such as values for each patient, by entering the values via the physician application program 218. The physician may specify, via the physician application program 218, different data collection parameters for different time periods of a day, different days or any other specified time periods. Similarly, through the physician application program 218, the physician may alter threshold values, against which the data analyzer 212 compares collected data. Optionally or alternatively, which set of data collection parameters, i.e., which row of the table 700, is used may depend in part or in whole on the amount of charge remaining in the battery that powers the transceiver assembly 203, the sensors 200 (if there is a separate battery for the sensors) and/or the long-range wireless transceiver 104. Less remaining charge may cause selection of a lower setting in the table 700.

In some embodiments, data collection and/or transmission parameters may be automatically changed in response to automatically detecting a measured physiologic data value exceeding or falling below a predetermined threshold. For example, if respiration rate, SpO2 or blood pressure exceeds a high-limit threshold or falls below a low-limit threshold, the remote server 107 can instruct the transceiver assembly 203 to increase the rate at which data is sampled from the sensors 200 and/or transmitted as less detailed data 106 or more detailed data 115 to the remote server 107. Similarly, the data sampling resolution and data transmission rate (from the transceiver assembly 203) or other parameter (collectively referred to herein as "data collection parameters") may be increased.

Some or all of the thresholds may be predetermined or they may be specified on a per-patient basis by the physician via the physician application program 218. Optionally or alternatively, some or all of the thresholds may be automatically determined based on collected data. For example, if data collected from a patient indicates to the remote server 107 that the patient is exercising, i.e., if for example data from the accelerometers indicates body movements consistent with the patient performing jumping jacks or sit-ups, thresholds for respiration and heart rate may be automatically increased until after these movements cease to be detected, plus an optional rest period. FIG. 8 contains a table 800 that lists exemplary threshold values for several patient activity levels.

Optionally, after the metric that caused a data collection parameter to be increased returns to normal for at least a predetermined period of time, the data collection parameter may be returned to its original value or a value intermediate the increased value and its original value. The data collection parameter may be returned to its original value in timed stages or stages based on measured data values.

The anomaly that triggers request 112 for retrospective data or a change in the data collection parameters may be more complex than a measured value exceeding or falling below a threshold value. In some embodiments, an automatically detected anomaly in the measured ECG automatically triggers the request 112 for retrospective data or altering one or more data collection parameters. For example, the ECG data may be processed by the data analyzer 212 to automatically classify heartbeats using morphology and heartbeat interval features, as described by Philip de Chazal, et al., in "Automatic Classification of Heartbeats Using ECG Morphology and Heartbeat Interval Features," IEEE Transactions on Biomedical Engineering, Vol. 51, No. 7, July, 2004, the contents of which are hereby incorporated by reference. In other words, collected data may be processed, before a determination is made whether an anomaly has been detected.

As noted, arrhythmia may be suspected or verified (or both) using ECG data, non-ECG data or a combination thereof. For example, an arrhythmia may be suspected or verified, based in whole or in part on respiration rate. The respiration rate may be determined based on data from one or more accelerometers in the sensors attached to the torso of the patient, as shown for example in FIG. 3. Chest movements detected by the accelerometers may be filtered, such as within expected frequencies and amplitudes, to derive the respiration rate. For example, one accelerometer may be included in in the sensor 309 (FIG. 3), which is located adjacent the patient's diaphragm, and another accelerometer may be include in the sensor 300 or 303. Relative motion between the two locations on the torso 312 represented by the two accelerometers closely represents diaphragm movement and, therefore, breathing.

Figure 9:
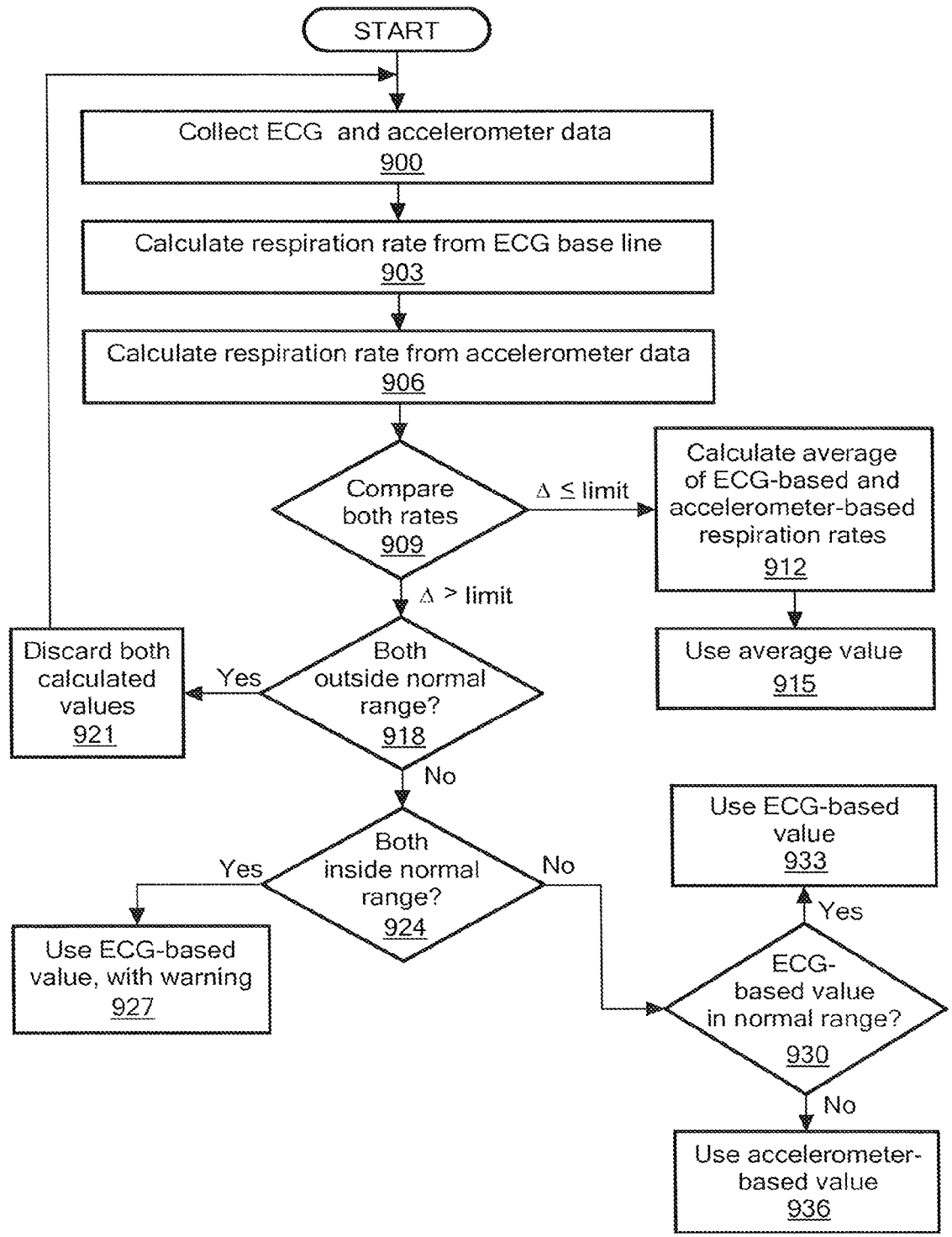
FIG. 9 is a flowchart illustrating a process for calculating a respiration rate, according to an embodiment of the present invention.

The respiration rate may also, or alternatively, be derived from ECG baseline data, as is well known in the art. Either of these respiration rates may be used by the data analyzer 212. However, some embodiments use both derived rates, as shown in a flowchart in FIG. 9. At 900, ECG and accelerometer data are collected. At 903, a first candidate respiration rate is calculated, based on the ECG baseline data, and at 906, a second candidate respiration rate is calculated, based on the accelerometer data. These two candidate rates are compared at 909. If the difference between the two candidate rates is less than a predetermined value, such as about 10%, an average of the two candidate rates is calculated at 912, and this average is used 915 by the data analyzer 212. Optionally, the maximum allowable difference between the two candidate rates, i.e., the limit in 909, may be specified by the physician via the physician application program 218.

However, if the two candidate rates differ by more than the predetermined value, control passes to 918. If both candidate rates are outside a predetermined range of normal respiration rates, both candidate rates are discarded 921, and the procedure loops back to 900. If both candidate rates are not outside the predetermined range of normal respiration rates, i.e., if at least one of the candidate rates is within the range, control passes to 924.

At 924, if both candidate rates are within the predetermined normal range, the ECG-based candidate respiration rate is used at 927. However, if only one of the candidate rates is within the predetermined normal range, control passes to 930.

At 930, if only the ECG-based candidate respiration rate is within the predetermined normal range, the ECG-based candidate respiration rate is used at 933. However, at 930, if the ECG-based candidate respiration rate is not within the predetermined normal range, the accelerometer-based candidate respiration rate is used at 936.

Figure 10:
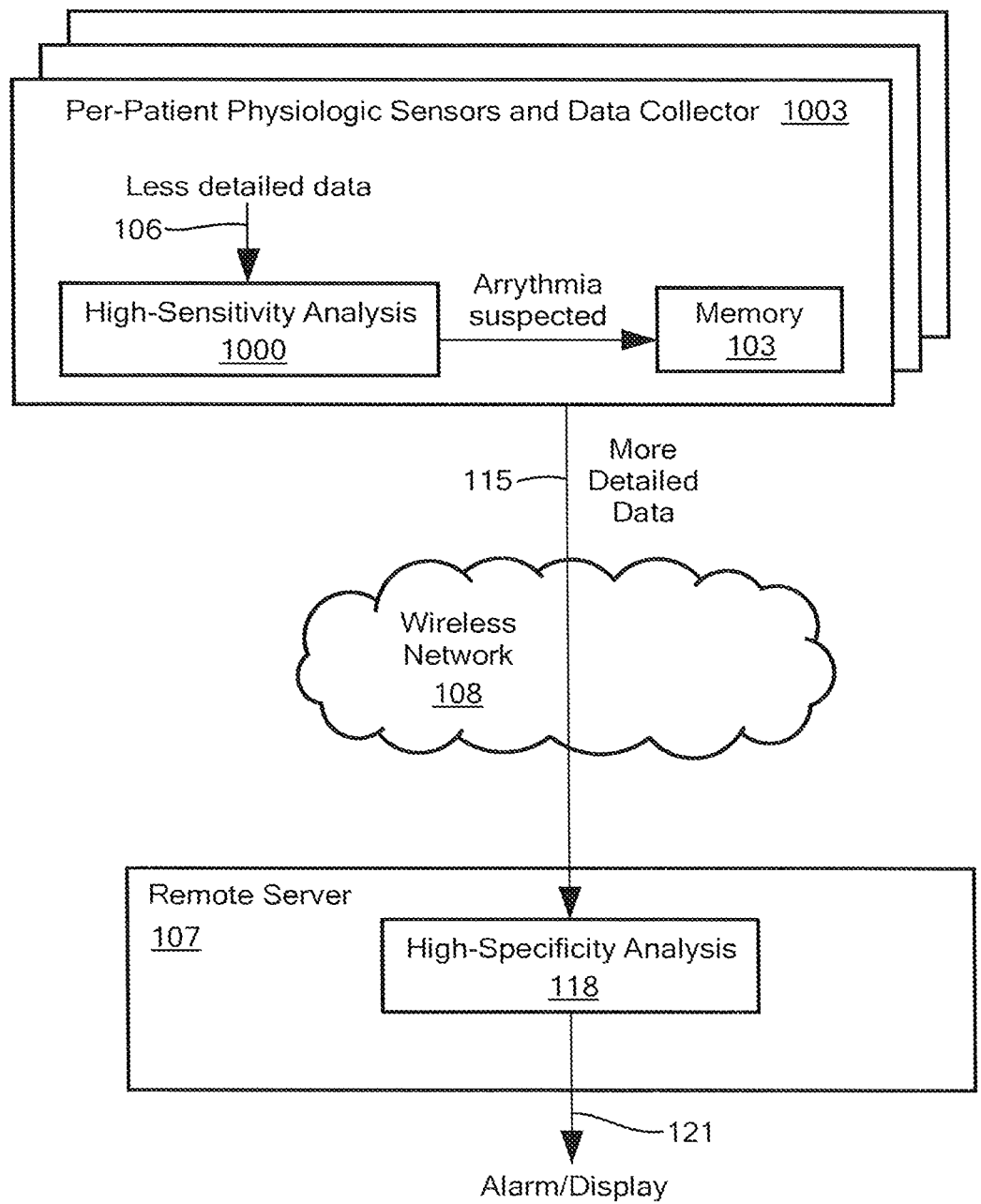
FIG. 10 is a schematic block diagram of an embodiment of the present invention.

Although embodiments in which all the data analysis is performed by the remote server 107 (FIG. 2) have been described, the high-sensitivity analysis 109 (FIG. 1) may optionally or alternatively be performed by the controller 206 or the cellular transceiver 104, i.e., at the patient, rather than in the remote server 107, as schematically illustrated in FIG. 10. In this case, if an arrhythmia is suspected by the high-sensitivity analysis 1000, no request signal needs to be sent to the per-patient physiologic sensors and data collector 1003. Instead, the controller 206 (see FIG. 2) or the cellular transceiver 104 (see FIG. 2) automatically sends the more detailed data to the remote server 107, and the remote server 107 performs the high-specificity analysis 118, as described above. In such an embodiment, the transceiver assembly 203 (see FIG. 2) may be referred to as a transmitter assembly, because it primarily or exclusively sends data to the remote server 107 and does not necessarily receive any requests 112 (See FIGS. 1 and 2) from the remote server 107.

Although embodiments of the present invention have been described as detecting and verifying suspected arrhythmias, other embodiments may be similarly configured and used to detect and verify other health or fitness conditions, such as inappropriate insulin level, respiration, blood pressure, SpO2, body movement, exertion and the like.

A remote health monitoring system includes a processor controlled by instructions stored in a memory. For example, the transceiver assembly may include and be controlled by such a processor, and the remote server may be controlled by another such processor. The memory may be random access memory (RAM), read-only memory (ROM), flash memory or any other memory, or combination thereof, suitable for storing control software or other instructions and data.

Some of the functions performed by the remote health monitoring system have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof.

Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks.

In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

The embodiments of the invention described above are intended to be merely exemplary. While the invention is described through the above-described exemplary embodiments, it will be understood by those of ordinary skill in the art that modifications to, and variations of, the illustrated embodiments may be made without departing from the inventive concepts disclosed herein. For example, although some aspects of remote health monitoring system have been described with reference to a flowchart, those skilled in the art should readily appreciate that functions, operations, decisions, etc. of all or a portion of each block, or a combination of blocks, of the flowchart may be combined, separated into separate operations or performed in other orders. Furthermore, disclosed aspects, or portions of these aspects, may be combined in ways not listed above. Accordingly, the invention should not be viewed as being limited to the disclosed embodiments.

What is claimed is:

1. A system for monitoring a patient, the system comprising:

a controller configured to communicate with at least one sensor coupled to a patient, the controller configured to receive physiologic data about the patient from the at least one sensor;
a memory configured to store the received physiologic data; and
a wireless transceiver coupled to the controller and configured to (a) transmit at a preset duty cycle, to a remote server, a subset of the received physiologic data regardless of whether the subset is indicative of a health-related anomaly; (b) receive from the remote server a signal based on the remote server determining that the subset of the received physiologic data indicates a health-related anomaly; and (c) transmit a portion of the received physiologic data to the remote server, in response to the signal from the remote server,
wherein the remote server is configured to: (a) analyze the subset of the received physiologic data according to a first technique; and (b) analyze the portion of the received physiologic data according to a second technique, wherein the second technique has a higher specificity for the health-related anomaly than the first technique.

2. The system of claim 1, further comprising the at least one sensor configured to be coupled to the patient to generate physiologic data about the patient.

3. The system of claim 1, wherein the subset of the received physiologic data is characterized by at least one of: a lower resolution than the received physiologic data for a corresponding time period, a lower sampling rate than the received physiologic data for a corresponding time period, and having been received from a different sensor than the received physiologic data for a corresponding time period.

4. The system of claim 1, wherein the signal from the remote server is a request for the portion of the received physiologic data.

5. The system of claim 4, wherein the signal from the remote server identifies a time period surrounding a time period corresponding to the health-related anomaly.

6. The system of claim 1, wherein the controller, the memory, and the wireless transceiver are contained in one physical assembly.

7. The system of claim 6, wherein the physical assembly is a phone.

8. The system of claim 1, wherein the controller, the memory, and the wireless transceiver are contained in more than one physical assembly.

9. The system of claim 1, wherein the health-related anomaly is an arrhythmia.

10. A method for monitoring a patient, the method comprising:
receiving physiologic data about the patient from at least one sensor coupled to the patient;
storing the received physiologic data in a memory;
transmitting at a preset duty cycle, to a remote server, a subset of the received physiologic data regardless of whether the subset is indicative of a health-related anomaly;
receiving from the remote server a signal based on the remote server determining that the subset of the received physiologic data indicates a health-related anomaly; and
transmitting a portion of the received physiologic data to the remote server, in response to the signal from the remote server,
wherein the remote server: (a) analyzes the subset of the received physiologic data according to a first technique; and (b) analyzes the portion of the received physiologic data according to a second technique, wherein the second technique has a higher specificity for the health-related anomaly than the first technique.

11. The method of claim 10, wherein a controller receives the physiologic data, and wherein the controller is communicatively coupled to the at least one sensor.

12. The method of claim 11, wherein a wireless transceiver performs the transmitting steps, and the controller, the memory, and the wireless transceiver are contained in one physical assembly.

13. The method of claim 12, wherein the physical assembly is a phone.

14. The method of claim 11, wherein a wireless transceiver performs the transmitting steps, and the controller, the memory, and the wireless transceiver are contained in more than one physical assembly.

15. The method of claim 10, wherein the subset of the received physiologic data is characterized by at least one of: a lower resolution than the received physiologic data for a corresponding time period, a lower sampling rate than the received physiologic data for a corresponding time period, and having been received from a different sensor than the received physiologic data for a corresponding time period.

16. The method of claim 10, wherein the signal from the remote server is a request for the portion of the received physiologic data.

17. The method of claim 16, wherein the signal from the remote server identifies a time period surrounding a time period corresponding to the health-related anomaly.

18. The method of claim 10, wherein the health-related anomaly is an arrhythmia.

19. A system for monitoring a patient, the system comprising:
at least one sensor configured to be coupled to the patient to generate physiologic data about the patient;
a controller configured to communicate with the at least one sensor, the controller configured to receive physiologic data about the patient from the at least one sensor;
a memory configured to store the received physiologic data;
a wireless transceiver coupled to the controller and configured to (a) transmit at a preset duty cycle, to a remote server, a subset of the received physiologic data regardless of whether the subset is indicative of a health-related anomaly; (b) receive from the remote server a signal based on the remote server determining that the subset of the received physiologic data indicates a health-related anomaly; and (c) transmit a portion of the received physiologic data to the remote server, in response to the signal from the remote server, wherein the signal from the remote server identifies a time period surrounding a time period corresponding to the health-related anomaly; and
a remote server configured to:
analyze the subset of the received physiologic data according to a first technique; and
analyze the portion of the received physiologic data according to a second technique, wherein the second technique has a higher specificity for the health-related anomaly than the first technique.

20. The system of claim 19, wherein the subset of the received physiologic data is characterized by at least one of: a lower resolution than the received physiologic data for a corresponding time period, a lower sampling rate than the received physiologic data for a corresponding time period, and having been received from a different sensor than the received physiologic data for a corresponding time period.

21. The system of claim 19, wherein the controller, the memory, and the wireless transceiver are contained in one physical assembly.

22. The system of claim 21, wherein the physical assembly is a phone.

23. The system of claim 19, wherein the controller, the memory, and the wireless transceiver are contained in more than one physical assembly.

24. The system of claim 19, wherein the health-related anomaly is an arrhythmia.

* * * * *